US011833083B2

(12) United States Patent
Horvath et al.

(10) Patent No.: US 11,833,083 B2
(45) Date of Patent: Dec. 5, 2023

(54) EYEWEAR WITH INTEGRALLY FORMED BARRIER

(71) Applicant: Oakley, Inc., Foothill Ranch, CA (US)

(72) Inventors: Steven Roger Horvath, Long Beach, CA (US); Bryson Stewart, Aliso Viejo, CA (US)

(73) Assignee: Oakley, Inc., Foothill Ranch, CA (US)

( * ) Notice: Subject to any disclaimer, the term of this patent is extended or adjusted under 35 U.S.C. 154(b) by 0 days.

(21) Appl. No.: 17/068,225

(22) Filed: Oct. 12, 2020

(65) Prior Publication Data

US 2021/0186760 A1 Jun. 24, 2021

Related U.S. Application Data

(60) Provisional application No. 62/951,597, filed on Dec. 20, 2019.

(51) Int. Cl.
A61F 9/02 (2006.01)

(52) U.S. Cl.
CPC .............. *A61F 9/025* (2013.01); *A61F 9/026* (2013.01); *A61F 9/027* (2013.01)

(58) Field of Classification Search
CPC . A61F 9/02; A61F 9/025; A61F 9/026; A63B 33/002; A63B 33/004
See application file for complete search history.

(56) References Cited

U.S. PATENT DOCUMENTS

| | | | |
|---|---|---|---|
| 4,709,696 A | 12/1987 | Angell | |
| 5,048,129 A | 9/1991 | Kamata | |
| 5,455,639 A * | 10/1995 | Magdelaine | G02C 11/12 351/44 |
| 5,802,620 A | 9/1998 | Chiang | |
| 6,192,523 B1 | 2/2001 | Pan | |
| 6,637,877 B1 | 10/2003 | Hartley et al. | |
| 6,676,257 B2 | 1/2004 | Sheldon et al. | |
| 7,143,454 B2 * | 12/2006 | Kawashima | A63B 33/004 2/440 |
| 7,200,875 B2 | 4/2007 | Dondero | |
| 7,290,294 B2 * | 11/2007 | Kita | A61F 9/025 2/443 |

(Continued)

FOREIGN PATENT DOCUMENTS

| | | |
|---|---|---|
| CN | 201823246 U | 5/2011 |
| DE | 202016106100 U1 | 4/2017 |

(Continued)

OTHER PUBLICATIONS

Extended European Search Report in European Application No. 20201262.1, dated Apr. 21, 2021 (7 pages).

*Primary Examiner* — F Griffin Hall
(74) *Attorney, Agent, or Firm* — Sterne, Kessler, Goldstein & Fox P.L.L.C.

(57) ABSTRACT

Eyewear, such as a goggle, includes a movable unitary lens and a chassis. The movable unitary lens includes an interior surface. The chassis includes a body that defines a central opening, and the body is configured to be worn on the face of a wearer. The chassis further includes a barrier that is integrally formed with the body, and the barrier includes an exterior surface that contacts the interior surface of the lens along a perimeter of the lens so as to form a seal with the lens.

25 Claims, 15 Drawing Sheets

(56) References Cited

U.S. PATENT DOCUMENTS

| | | | |
|---|---|---|---|
| 7,797,765 B2 * | 9/2010 | Musal | A61F 9/025 |
| | | | 2/448 |
| 7,856,673 B2 | 12/2010 | Reed | |
| 8,850,626 B2 | 10/2014 | Reyes et al. | |
| 8,881,316 B2 | 11/2014 | Reyes et al. | |
| 9,192,520 B2 | 11/2015 | Cater et al. | |
| 2006/0242745 A1 | 11/2006 | DiChiara | |
| 2011/0016595 A1 | 1/2011 | Brace et al. | |
| 2012/0284907 A1 * | 11/2012 | Shiue | B63C 11/12 |
| | | | 2/431 |
| 2014/0063438 A1 * | 3/2014 | Cater | G02C 5/12 |
| | | | 351/62 |
| 2016/0143784 A2 | 5/2016 | Arnette | |
| 2017/0100286 A1 | 4/2017 | Salmini et al. | |
| 2017/0203159 A1 * | 7/2017 | Schuwerk | A63B 33/004 |

FOREIGN PATENT DOCUMENTS

| | | |
|---|---|---|
| EP | 0 827 761 B1 | 7/2002 |
| EP | 3470028 P | 4/2019 |
| WO | 2014201500 A1 | 12/2014 |

* cited by examiner

EYEWEAR WITH INTEGRALLY FORMED BARRIER

CROSS-REFERENCE TO RELATED APPLICATION

This application claims the benefit of U.S. Provisional Application No. 62/951,597 filed Dec. 20, 2019, which is incorporated herein by reference in its entirety.

FIELD

Embodiments described herein generally relate to eyewear. Specifically, embodiments described herein relate to a goggle having an integrally formed barrier.

BACKGROUND

A goggle is a type of eyewear that typically covers a significant portion of the face of the user beyond the eyes. A goggle is usually formed to follow the contour of the wearer's face for better protection of the wearer's eyes and face. This type of eyewear is usually designed for activities that require increased protection of the wearer's eyes and face such as snow sports, motorcycle racing, and bicycle racing.

A typical goggle includes a transparent lens that is supported by a frame. The frame provides structural support to the lens and can surround the edge of the lens. The goggle may be constructed by forming and arranging a gasket between the frame and lens along a perimeter of the lens. The gasket forms a seal that prevents moisture and particulate matter from passing beyond the lens and contacting the wearer's face and eyes.

Typically, the gasket may be formed by cutting the gasket from a block or sheet of foam. For example, the gasket may be formed from a urethane foam, such as Poron®. Cutting the gasket from a block of foam may result in considerable waste of the unused portion of the block of foam, which may not readily be used or recycled due to the shape of the gasket.

BRIEF SUMMARY OF THE INVENTION

Some embodiments described herein relate to a goggle that may include a movable unitary lens having an interior surface, and a chassis. The chassis of the goggle may include a body defining a central opening wherein the body is configured to be worn on a wearer's face and a barrier integrally formed with the body. The barrier of the chassis of the goggle may have an exterior surface configured to contact the interior surface of the lens along a perimeter of the lens so as to form a seal with the lens.

In any of the various embodiments described herein, the barrier may include a blade connected to and extending from an inner edge of the body proximal to the central opening toward an outer edge of the body distal to the central opening, and the blade may contact the interior surface of the lens.

In any of the various embodiments described herein, the blade may extend from an exterior facing side of the body of the chassis at an angle relative to a vertical axis of the goggle, such that the angle may be in a range from approximately 15 degrees to approximately 45 degrees.

In any of the various embodiments described herein, the barrier has a thickness of 0.5 mm to 1 mm as measured from the exterior surface of the barrier to an interior surface of the barrier.

In any of the various embodiments described herein, the chassis may include an elastomer.

In any of the various embodiments described herein, the chassis may include a thermoplastic polyurethane.

In any of the various embodiments described herein, the chassis may include a material having a Shore A hardness range of approximately 70 to approximately 100.

In any of the various embodiments described herein, the barrier may have a first and second ridge on the exterior surface of the barrier, such that the first and second ridges are each configured to contact the interior surface of the lens.

In any of the various embodiments described herein, the barrier may include a tip that is rounded.

In any of the various embodiments described herein, the chassis may include a chassis material, and the goggle may further include a frame connected to the chassis, wherein the frame may be formed of a frame material that is more rigid than the chassis material. In some embodiments, the chassis may be overmolded onto the frame.

In any of the various embodiments described herein, the lens may be fully removable from the frame.

In any of the various embodiments described herein, the goggle may further include a frame connected to the chassis, and a locking assembly configured to secure the lens to the frame. In some embodiments, the locking assembly may be the frame, and the lens may be secured to the frame by an interference fit.

In any of the various embodiments described herein, the barrier may be compressed by the lens.

In any of the various embodiments described herein, the chassis may support the lens.

Some embodiments described herein relate to a goggle that may include a frame including a frame material, a movable unitary lens having an interior surface and an exterior surface, and a chassis including a chassis material that is less rigid than the frame material. The chassis of the goggle may include a body defining a central opening, wherein the body is configured to be worn on a face of a wearer. The chassis of the goggle may further include a barrier integrally formed with the body, and the barrier of the chassis of the goggle may include a blade having an exterior surface that contacts the interior surface of the lens so as to form a seal with the lens.

In any of the various embodiments described herein, the goggle may further include a locking assembly configured to secure the movable unitary lens to the frame.

In any of the various embodiments described herein, the blade may be arranged between the lens and the body of the chassis.

In any of the various embodiments described herein, the chassis may be overmolded onto the frame.

In any of the various embodiments described herein, the lens of the goggle may include two or more layers.

In any of the various embodiments described herein, the chassis material may include an elastomer.

In any of the various embodiments described herein, the chassis material may include a thermoplastic polyurethane.

In any of the various embodiments described herein, the barrier may extend along a perimeter of the lens. In some embodiments, the barrier may extend along the entire perimeter of the lens.

BRIEF DESCRIPTION OF THE DRAWINGS/FIGURES

The accompanying drawings, which are incorporated herein and form a part of the specification, illustrate the present disclosure and, together with the description, further serve to explain the principles thereof and to enable a person skilled in the pertinent art to make and use the same.

DETAILED DESCRIPTION OF THE INVENTION

Embodiments of the present disclosure will now be described in detail in the accompanying drawings. References to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As discussed in the Background, goggles typically use a separately formed gasket for providing a seal between a lens and a frame of the goggle. The use of a separate gasket adds complexity to the manufacturing process by requiring an extra component to be formed and assembled with the frame and lens. Further, the use of a separate gasket increases the expense of manufacturing the goggle.

Accordingly, embodiments of the present disclosure provide a goggle having a chassis with an integrally formed barrier. By forming the barrier as part of the chassis, the manufacturing process is simplified because the chassis and barrier are formed in a single step and there is no need to secure a separate gasket to the chassis. The integrally formed chassis and barrier can maintain a seal between the lens and chassis, preventing or inhibiting moisture and particulate matter from passing around lens and contacting the wearer's face and/or eyes.

As used herein, the term "horizontal" refers to a direction substantially parallel to a line extending between the eyes of a wearer. As used herein, the term "vertical" refers to a direction substantially perpendicular to the horizontal direction and along an eyewear's lens's surface.

Figure 1:
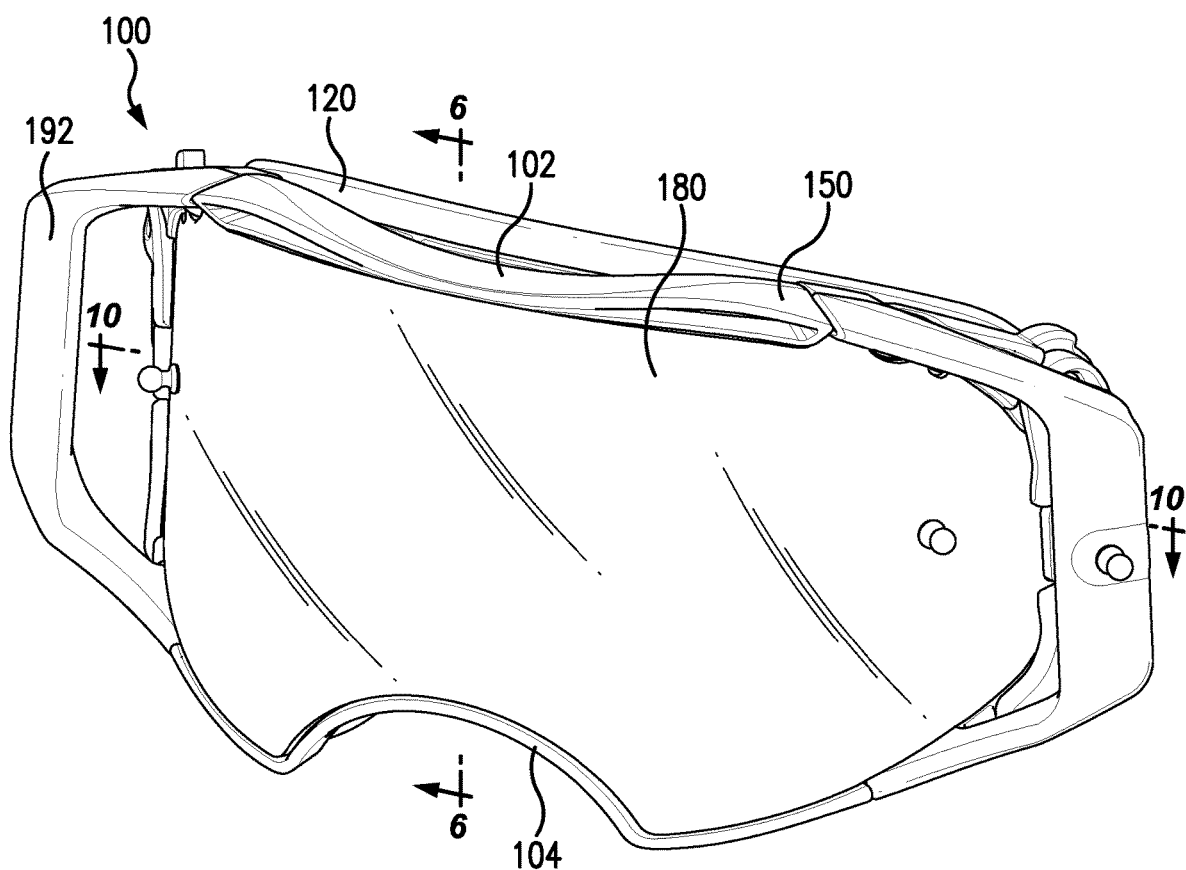
FIG. 1 shows a perspective view of a goggle according to an embodiment.

FIG. 1 shows a goggle 100 having an integrally formed barrier according to an embodiment. Goggle 100 may be used for activities where eye protection is desired, such as motocross, snowboarding, or skiing, among others. Goggle 100 may include a lens 180 that covers a field of view of a wearer. Lens 180 may be movably securable to a frame 150 of goggle 100. Frame 150 may provide goggle 100 with structural support and impact-resistance. For example, opposing sides of lens 180 may be secured to opposing sides of frame 150 via an interference fit with frame 150, or via a locking assembly 170, as described in further detail herein. In an aspect, lens 180 may be secured to frame 150 only at sides of lens 180 so that lens 180 is not secured to frame 150 about an entire perimeter 185 of lens 180. This may help to allow lens 180 to bend or flex when goggle 100 is worn by a wearer. Frame 150 is configured to support lens 180 in the wearer's field of view. A chassis 120 may be connected to frame 150 of goggle 100, and chassis 120 is configured to be compliant so as to fit closely to a face of a wearer. Chassis 120 is configured to form a seal with lens 180. In some embodiments chassis 120 may be overmolded onto frame 150. However, chassis 120 may alternatively be connected to frame 150 via interference fit, mechanical fasteners, or adhesives, among other fastening methods.

Lens 180 may be a unitary lens 180, such that a single lens 180 covers both eyes of the wearer. However, in some embodiments, lens 180 may be a dual lens with one lens covering each eye of the wearer. In some embodiments, lens 180 may include a single layer, or may include multiple layers. In some embodiments, lens 180 may be a laminated lens 180 formed by a series of stacked layers. In some embodiments, layers of lens 180 may include an outer layer and an inner layer that are separated by a space. The space may be filled with air or another gas to provide an air gap for thermal insulation.

Lens 180 includes an exterior surface 181 facing away from a wearer when goggle 100 is worn, and an opposing interior surface facing toward a wearer's face when goggle 100 is worn. In some embodiments, lens 180 may have a curvature, and an interior surface of lens 180 may have a concave curvature so as to contour to a shape of a wearer's face or head. Lens 180 may be spaced from a wearer's eyes and face so as to define a zone that is protected from moisture and particulate matter when goggle 100 is worn.

Lens 180 may be formed from any of various transparent materials, such as glass, for example a silicate glass, polycarbonate, polymethylmethacrylate, among other transparent materials. Lens 180 may be formed from a material that is strong, durable, and/or impact-resistant so that lens 180 does not readily crack or break and can withstand impact. In some embodiments, lens 180 may include a coating on an exterior surface and/or interior surface of lens 180, such as an anti-reflective coating, an anti-glare coating, or a UV-protective coating, among others.

In some embodiments, lens 180 may be movable. A goggle having a movable lens is described, for example, in U.S. Pat. Nos. 7,200,875 and 9,192,520, which are each incorporated herein by reference in their entirety. Lens 180 may be movably attached to frame 150 or chassis 120 of goggle 100 so as to slide or pivot relative to frame 150 or chassis 120 for controlling ventilation. In some embodiments, lens 180 is fully removable from frame 150 or chassis 120 so that lens 180 may be replaced. Because lens 180 is removable, lens 180 may be interchanged with other lenses. Thus, lens 180 may be replaced if broken, cracked, or otherwise damaged without having to replace goggle 100 in its entirety. Further, a wearer may desire to interchange lenses 180 that have different properties. For example, a first lens 180 may be tinted or may have an anti-glare coating for use on bright days, while a second lens 180 may have multiple layers so as to provide improved thermal insulation. Further, a wearer may simply wish to interchange lenses 180 for aesthetic purposes to provide goggle 100 with a desired appearance. Additionally, lens 180 may be removable such that the wearer may be able to remove lens 180 without removing goggle 100 from the wearer's head.

In some embodiments, goggle 100 may include a frame 150. Frame 150 may provide structural support to goggle 100. Frame 150 may be shaped similarly to a perimeter 185 of lens 180 when viewed from the front, and may be connected to chassis 120 around a perimeter of chassis 120. In some embodiments, frame 150 may be configured to secure lens 180. When lens 180 is secured to frame 150, interior surface 182 of lens 180 is in contact with chassis 120, and frame 150 maintains lens 180 in position in a wearer's field of view. In some embodiments, frame 150 may include various additional components of goggle 100, such as one or more of outriggers 192, a strap, a nose guard, and a locking assembly 170, among other components.

Frame 150 may be connected to chassis 120 of goggle 100. Chassis 120 may be overmolded onto frame 150, or chassis 120 and frame 150 may be separate components that are assembled along with lens 180 during the manufacture of goggle 100. Chassis 120 may be secured to frame 150 for example via a snap fit, press fit, interference fit, or chassis 120 and frame 150 may include mating components. In some embodiments, for example, body 122 of chassis 120 may include a recess 127 configured to receive a protrusion 152 of frame 150 (see, e.g., FIG. 6). Chassis 120 may be permanently secured to frame 150 such as by the use of mechanical fasteners, epoxy or adhesives, among other types of fasteners or fastening methods.

Frame 150 may be formed of a frame material that differs from chassis material used to form chassis 120. Frame material may include, for example, a nylon polymer, such as TR90 nylon. In some embodiments, frame material may be a high durometer rubber relative to the chassis material. In an aspect, frame material may have a greater rigidity than the chassis material, so that frame 150 is more rigid and less flexible than chassis 120. Thus, frame 150 can provide structural support to goggle 100 and helps goggle 100 maintain its shape. Further, frame 150 may help to maintain proper lens curvature so as to preserve optics of goggle 100. A goggle having a frame made of a material that is more rigid than a material of a chassis is described, for example in U.S. Pat. No. 8,881,316, which is incorporated herein by reference in its entirety.

Chassis 120 may be shaped so as to contour to a wearer's face. For example, an upper end 102 of chassis 120 may extend across a forehead of a wearer, a lower end 104 of chassis 120 may extend over a wearer's cheeks and nose, and sides of chassis 120 extend along the sides of the wearer's face so as to connect upper end 102 and lower end 104 of chassis 120. Chassis 120 may be shaped similarly to an outer perimeter 185 of lens 180 as chassis 120 is configured to contact an interior surface 182 of lens 180 around at least a portion of a perimeter 185 of lens 180. Chassis 120 defines a central opening 125 configured to be covered by lens 180. Chassis 120 may be arranged between frame 150 and lens 180.

In some embodiments, goggle 100 may have a frameless construction and does not include a frame 150. In such embodiments, goggle 100 may include a chassis 120 and a lens 180, and lens 180 may have sufficient structural rigidity to serve as the main structural support of goggle 100. In such embodiments, in addition to fitting to a wearer's face and forming a seal with lens 180, chassis 120 may serve to support lens 180 and other components of goggle 100. For example, chassis 120 may include a locking assembly for securing lens 180, and in some embodiments, locking assembly may include magnetic fasteners or mechanical fasteners, among other fastening mechanisms for securing lens 180 to chassis 120. In such embodiments, chassis 120 may include various additional components of goggle 100, such as one or more of outriggers 192, a strap, a nose guard, and a locking assembly 170 as described herein, among other components.

Figure 2:
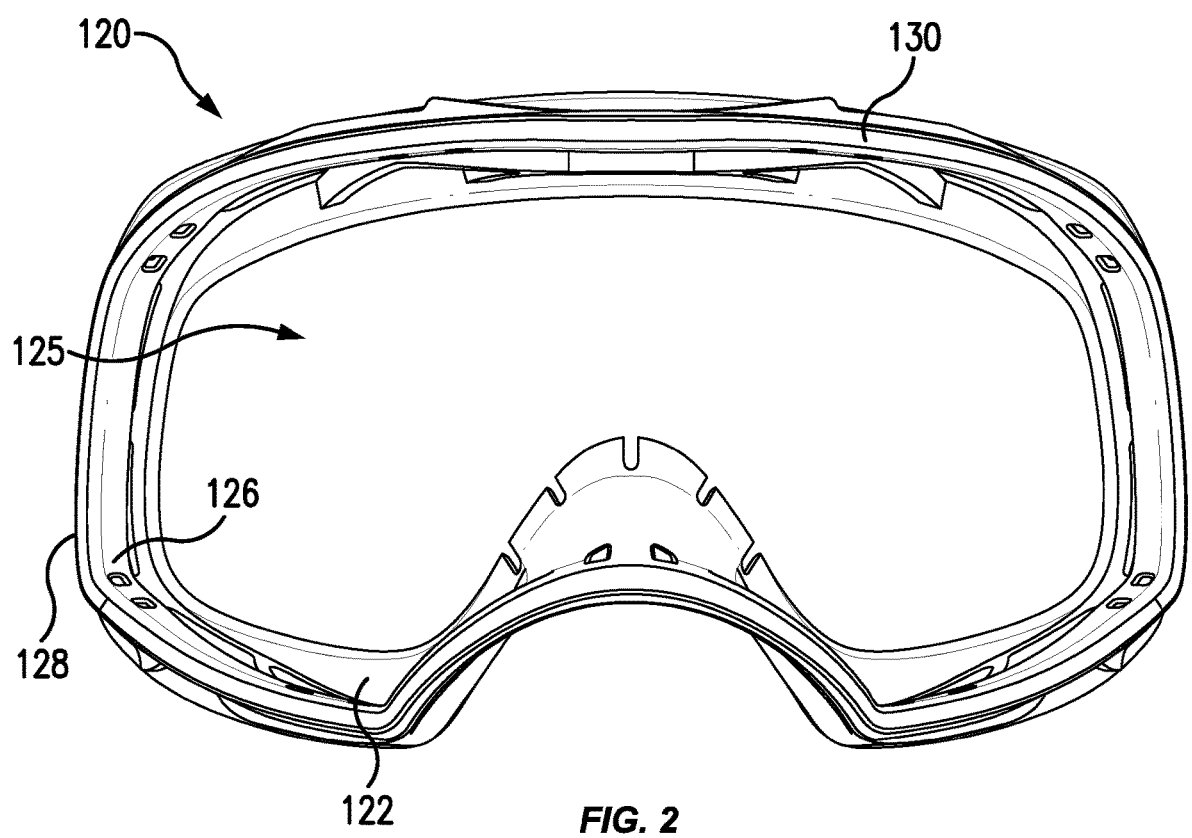
FIG. 2 shows a front perspective view of a chassis of the goggle of FIG. 1.
Figure 3:
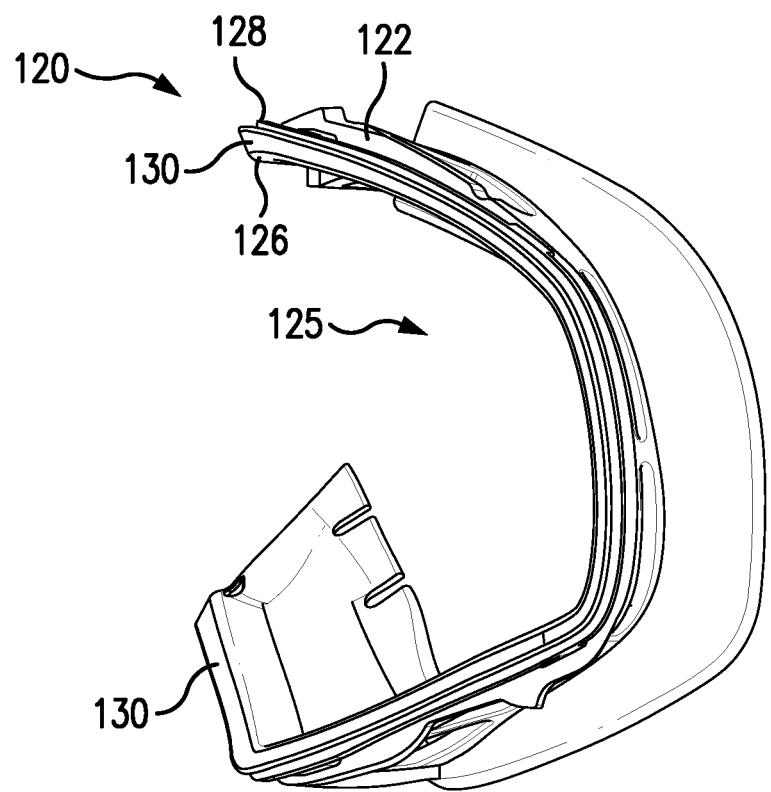
FIG. 3 shows a side view of the chassis of the goggle of FIG. 1.

In some embodiments, chassis 120 of goggle 100 can include a body 122 and a barrier 130, as shown in FIGS. 2 and 3. Body 122 and barrier 130 of chassis 120 are integrally formed so that chassis 120 has a unitary construction and is formed as a single piece. Forming the integral barrier 130 removes the need for a separate gasket that must be assembled, thus simplifying manufacture of goggle 100. Chassis 120 may be formed, for example, by molding, such as by injection molding, compression molding, or transfer molding, among other molding methods. In some embodiments, chassis 120 may be formed by additive manufacturing methods (e.g., 3-D printing).

Body 122 of chassis 120 may have an exterior facing side 121 that faces away from a wearer's face, and a body facing side 123 that faces toward a wearer's face when a goggle 100 is worn. In some embodiments, body facing side 123 may be placed in contact with wearer's face. Thus, body 122 of chassis 120 is configured to rest against a wearer's face, and barrier 130 is configured to contact lens 180 of goggle 100. Further, in embodiments having a frame 150, body 122 may be connected to frame 150 of goggle 100. Body facing side 123 of chassis 120 may be curved and may have a concave curvature so as to contour to a shape of a wearer's head.

Figure 4:
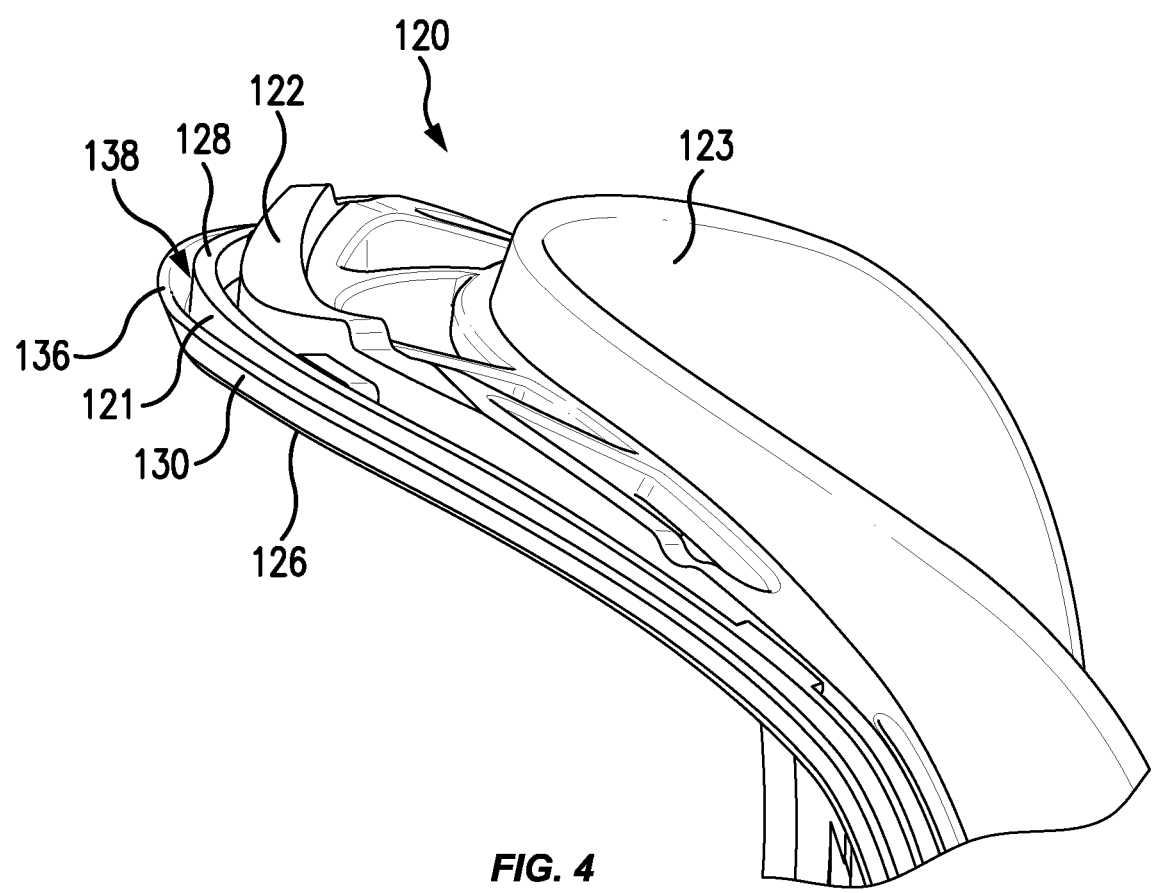
FIG. 4 shows a close-up perspective view of an upper end of the chassis of the goggle of FIG. 1.

Barrier 130 of chassis 120 is integrally formed with and extends from body 122 of chassis 120, as shown for example in FIG. 4. Barrier 130 may extend from an exterior facing side 121 of body 122 of chassis 120. Barrier 130 may extend from an entire perimeter of body 122 of chassis 120 (see, e.g., FIG. 2).

Figure 5:
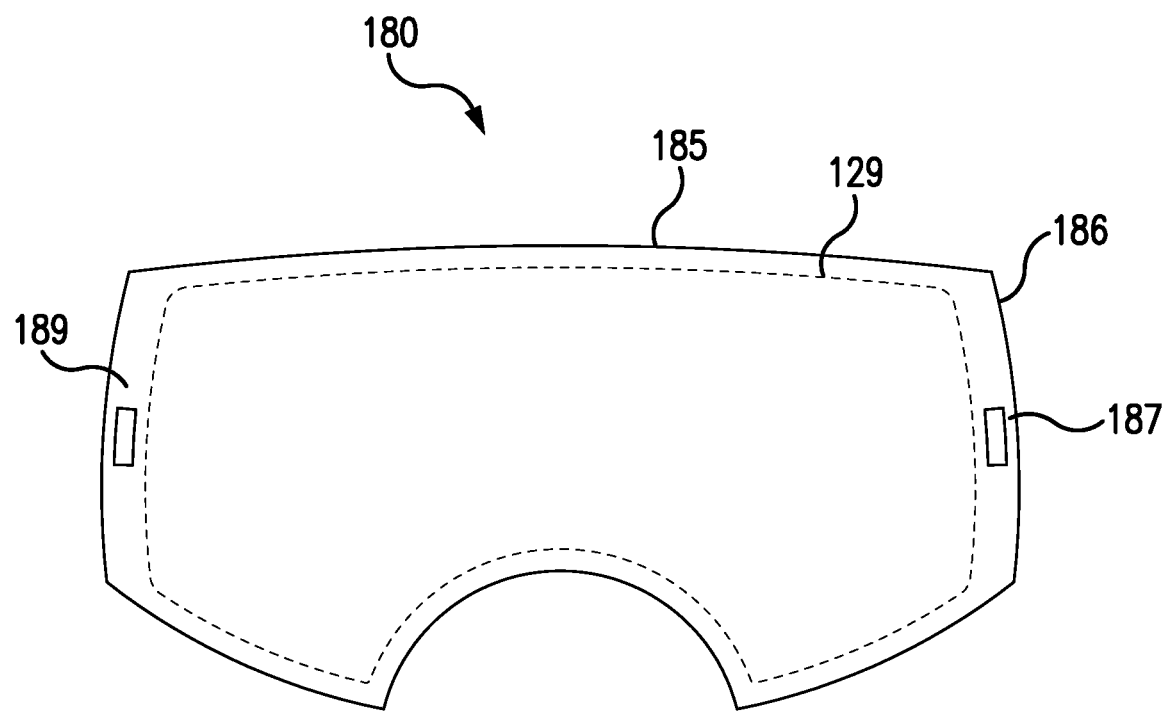
FIG. 5 shows a front view of a lens of a goggle according to an embodiment showing a location at which a chassis of goggle contacts the lens.

In some embodiments, barrier 130 may touch interior surface 182 of lens 180 adjacent outer perimeter 185 of lens 180. Outer perimeter 185 of lens 180 may be defined as an outermost boundary of lens 180. Barrier 130 may contact an interior surface of lens 180 adjacent to at least a portion of outer perimeter 185 of lens 180. In some embodiments, barrier 130 may contact lens 180 along substantially an entire perimeter 185 of lens 180. In such embodiments, barrier 130 may contact interior surface of lens 180 along perimeter 185 except in locations where it is desired to provide vents or venting. Barrier 130 may contact lens 180 at boundary 129, as shown in FIG. 5. Boundary 129 is inward of perimeter 185 of lens 180 and generally follows perimeter 185 of lens 180. For example, boundary 129 may be arranged at a distance of 1 mm to 15 mm inward of outer perimeter 185 of lens 180. In this way, barrier 130 may form a seal with lens 180 along boundary 129 at which barrier 130 contacts lens 180. Boundary 129 may be further spaced from outer perimeter 185 at sides 187, 189 of lens 180. For example, boundary 129 may be spaced from outer perimeter 185 at sides 187, 189 of lens 180 by 8 mm to 15 mm, so as to allow space for connection of lens 180 to frame 150 at sides 187, 189 of lens 180.

In some embodiments, barrier 130 contacts only an interior surface 182 of lens 180. In some embodiments, barrier 130 contacts only an interior surface 182 of lens 180 and a perimeter edge 186 of lens 180. Perimeter edge 186 may be defined as an edge of lens 180 between interior surface 182 and exterior surface 181 of lens 180 at perimeter 185 of lens 180. In such embodiments, barrier 130 does not contact an exterior surface 181 of lens 180. Thus, barrier 130 does not contact both surfaces of lens 180 and does not wrap around or grip perimeter edge 186 of lens 180. Barrier 130 does not serve as a clamp or bracket to secure lens 180, and instead lens 180 may be secured to frame 150 (or chassis 120 in frameless embodiments) of goggle 100 by a locking assembly, such as magnetic fasteners, mechanical fasteners, or locking assembly 170 (see, e.g., FIGS. 15 and 16), as discussed in further detail herein.

Figure 6:
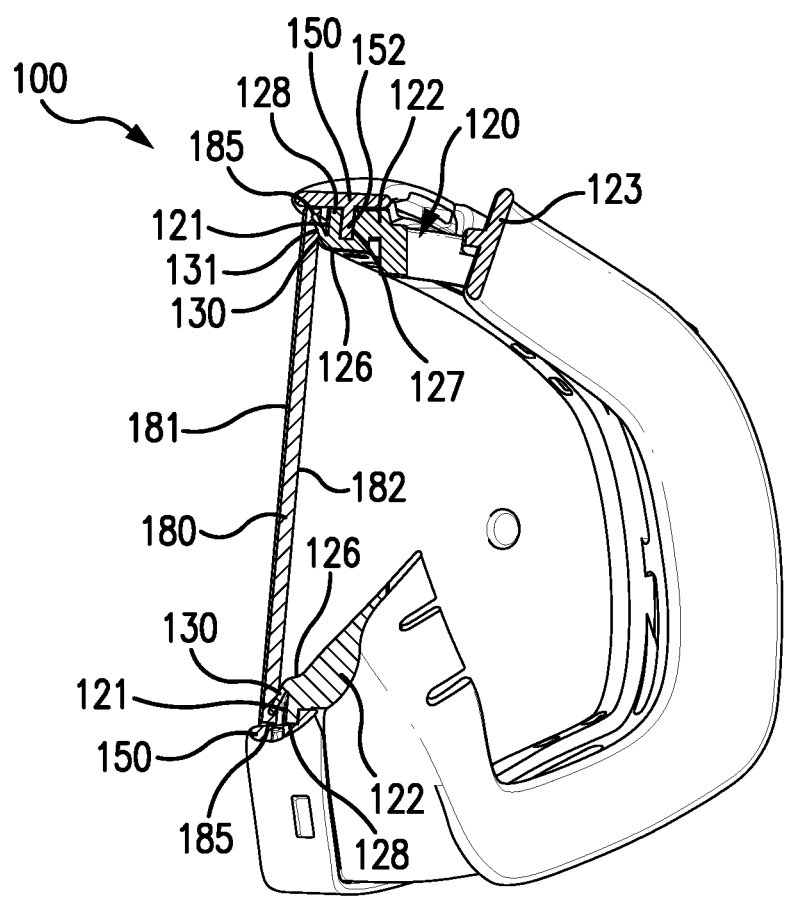
FIG. 6 shows a cross sectional view of the goggle of FIG. 1 taken along line 6-6 as shown in FIG. 1.

Barrier 130 may be connected to an inner edge 126 of body 122 adjacent to central opening 125 and may extend outwardly from exterior facing side 121 of body 122 in a direction toward outer edge 128 of body 122 away from central opening 125, as shown in FIG. 6. A channel 138 may be formed between barrier 130 and body 122 of chassis 120, and particularly between an exterior facing side 121 of body 122 and interior surface 132 of barrier 130. In some embodiments, channel 138 may have a V-shape. In some embodiments, however, barrier 130 may extend from exterior facing side 121 of body 122 of chassis 120 and may be connected to an outer edge 128 of body 122 rather than to inner edge 126 of body 122. In such embodiments, barrier 130 may extend in a direction from outer edge 128 toward inner edge 126 of body 122. Barrier 130 need not extend entirely from outer edge 128 to an inner edge 126 of body 122.

In some embodiments, barrier 130 may be formed as a blade 133, as shown in FIG. 6, and blade 133 may be substantially linear. However, in some embodiments, blade 133 may have a curvature. Blade 133 may include a tip 136 opposite end of blade 133 connected to body 122 of chassis 120. Tip 136 and/or an exterior surface 131 of barrier 130 may contact interior surface 182 of lens 180.

Figure 7:
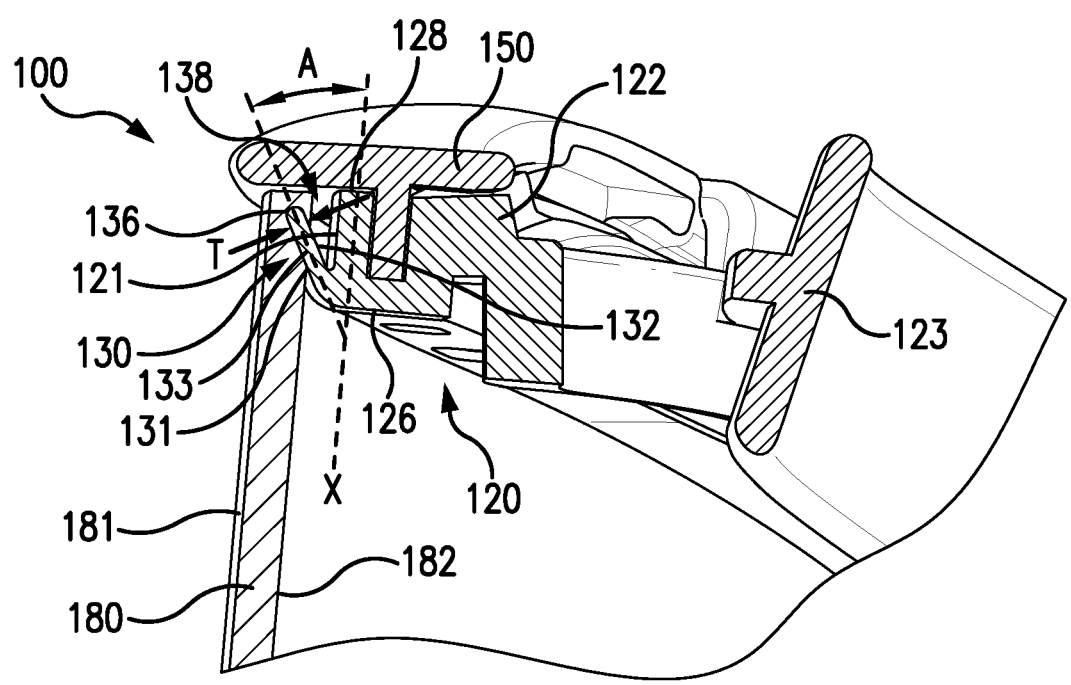
FIG. 7 shows a detailed cross sectional view of the upper end of the goggle as shown in FIG. 6.

Blade 133 may have a constant thickness along its length, where the thickness T is measured as a shortest distance from an exterior surface 131 to an interior surface 132 of blade 133, as shown in FIG. 7. In some embodiments, a maximum thickness of blade 133 may range from approximately 0.5 mm to approximately 1 mm. Blade 133 may have a thickness such that blade 133 may flex. As thickness of blade 133 increases, the flexibility of blade 133 decreases. Thus, thickness of blade 133 depends in part on the material used to form blade 133 as will be readily understood by one of ordinary skill in the art. In some embodiments, blade 133 may taper from body 122 toward tip 136 of blade 133 such that thickness decreases towards tip 136. In some embodiments, tip 136 may be rounded. However, in some embodiments, tip 136 of barrier 130 may taper toward a point, or may be squared.

Figure 10:
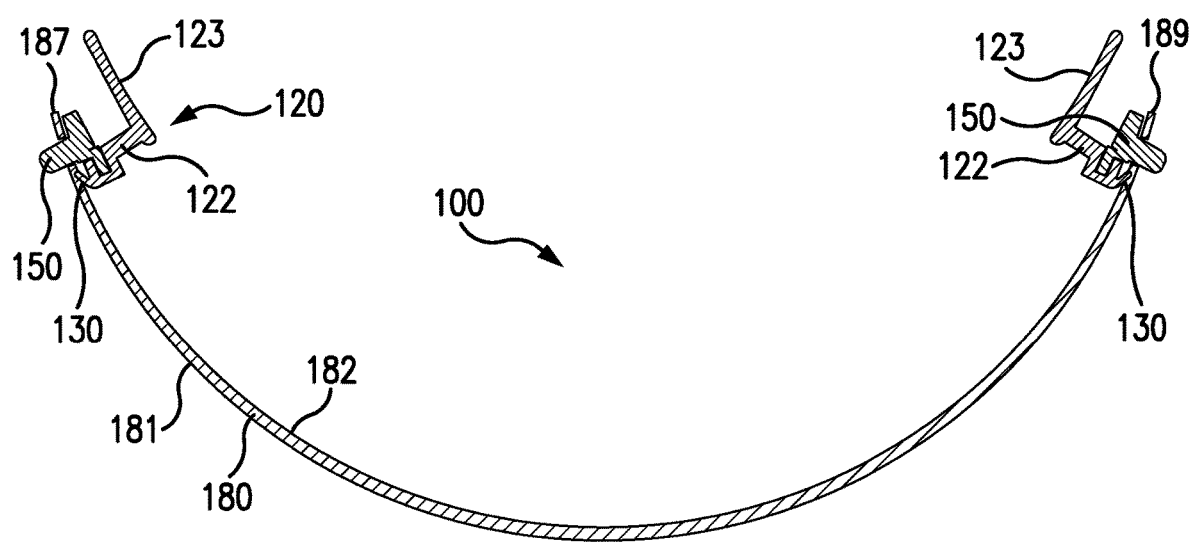
FIG. 10 shows a cross sectional view of the goggle of FIG. 1 taken along line 10-10 as shown in FIG. 1.

In some embodiments, barrier 130 may form an angle A relative to a vertical axis X of chassis 120 or goggle 100 when barrier 130 is in a resting or non-compressed state, as shown in FIG. 7. Angle A may range from approximately 15 degrees to approximately 45 degrees, approximately 20 degrees to approximately 40 degrees, or approximately 25 degrees to 35 degrees. Barrier 130 may extend along body 122 of chassis 120 so as to contact lens 180 about an entire perimeter 185 of lens 180. Angle A formed by barrier 130 may be constant about a perimeter of chassis 120 or may vary. For example, angle A may be relatively large at a central portion of chassis 120 and may be relatively small toward sides of chassis 120, as shown for example in FIG. 10.

Figure 8:
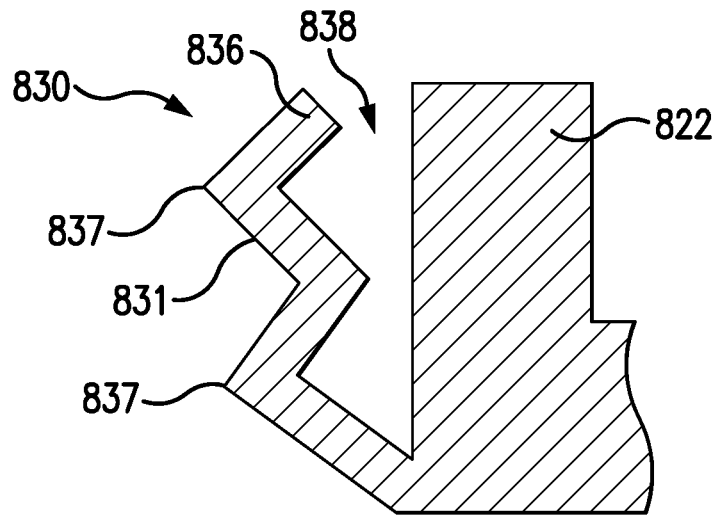
FIG. 8 shows a cross sectional view of a barrier according to an embodiment.

In some embodiments, barrier 830 may be non-linear, as shown for example in FIG. 8. Barrier 830 may have a chevron or inverted V-shaped pattern so as to form one or more peaks 837. In FIG. 8, barrier 830 is shown as having two peaks 837. In such embodiments, barrier 830 may have a M-shape (or W-shape), such that peaks 837 are formed on an exterior surface 831 of barrier 830. In this way, lens contacts peaks 837 of barrier 830 when lens is secured to frame of goggle. In such embodiments, barrier 830 is spaced from body 822 of chassis by a channel 838.

Figure 9:
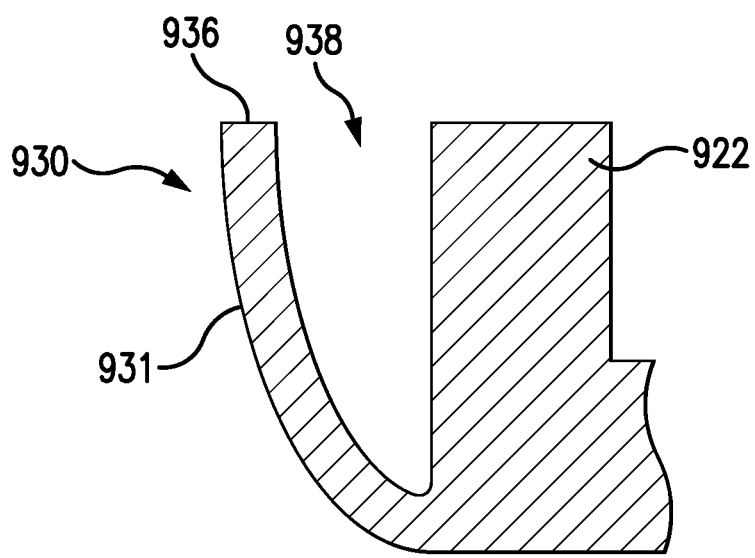
FIG. 9 shows a cross sectional view of a barrier according to an embodiment.

In some embodiments, barrier 930 may have a curvature, as shown for example in FIG. 9. Specifically, an exterior surface 931 of barrier 930 may be curved. Barrier 930 may be curved such that an end portion or tip 936 of barrier 930 is substantially parallel to body 922 of chassis, as shown in FIG. 9. In this way, lens may contact exterior surface 931 of barrier 930 along a length of barrier 930. Barrier 930 may be spaced from body 922 of chassis by a channel 938.

Figure 11:
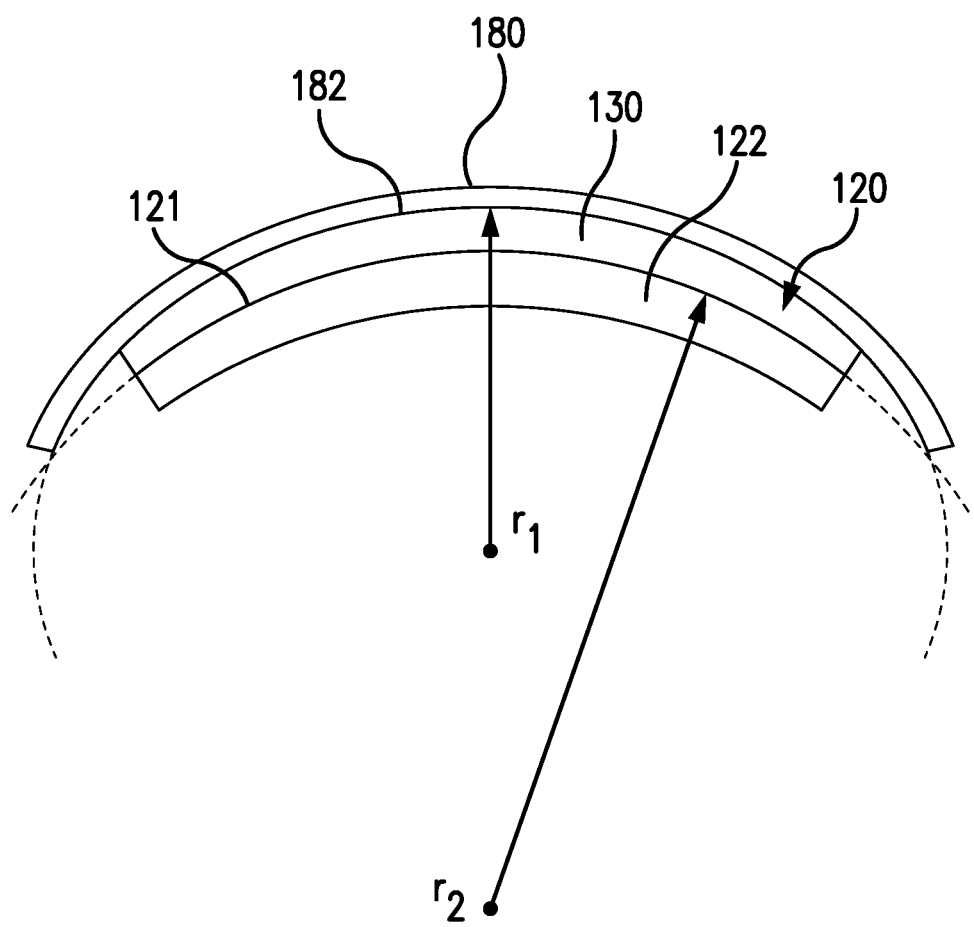
FIG. 11 shows a top down plan view of a chassis and a lens of a goggle according to embodiment.

Lens 180 and chassis 120 may be formed so as to have the same curvature so that lens 180 is in contact with chassis 120 along boundary 129 as shown in FIG. 5. However, due to manufacturing tolerances, and bending or deformation of chassis 120 or lens 180 during use of goggle 100, there may be some mismatch or separation of lens 180 and chassis 120, as shown in FIG. 11. For example, lens 180, and particularly an interior surface 182 of lens 180 may have a radius of curvature $r_1$ and chassis 120, particularly an exterior facing side 121 of chassis 120 may have a second radius of curvature $r_2$ that differs from $r_1$. The mismatch in the radius of curvature may result in a gap or separation in which moisture and particulate matter could pass behind lens 180. Barrier 130 of chassis 120 helps to account for such mismatches of lens 180 and chassis 120, as barrier 130 extends outward from exterior facing side 121 of body 122 of chassis 120 and may be compressed by lens 180. Barrier 130 may be under greater compression in locations at which there is little to no mismatch in the curvature of chassis 120 and lens 180 and may be compressed to a lesser degree in locations in which there is a mismatch of lens 180 and chassis 120. In this way, barrier 130 may fit closely against interior surface 182 of lens 180 along a perimeter 185 of lens 180. Lens 180 and chassis 120 may have a greater mismatch at a central portion of goggle 100 as lens 180 is secured to frame 150 only at sides of frame 150 and not along an entire perimeter 185 of lens 180.

When barrier 130 is compressed, barrier 130 bends or flexes so that interior surface 132 of barrier 130 moves toward exterior facing side 121 of body 122 of chassis 120, reducing the size of channel 138. The ability of barrier 130 to flex helps to prevent any breaks in the seal formed by contact of barrier 130 and lens 180. In this way, barrier 130 may help to form a seal to prevent moisture or particulate matter from passing around lens 180 and reaching a wearer's face and eyes. Barrier 130 may extend around an entire perimeter of body 122 so as to contact interior surface 182 of lens 180 and form a seal around an entire perimeter of lens 180.

In some embodiments, barrier 130 may have a length of approximately 1 mm to approximately 10 mm, approximately 2 mm to approximately 9 mm, or approximately 3 mm to approximately 8 mm. Length of barrier 130 is measured from a point of connection of barrier 130 to body 122 to a tip 136 of barrier 130 along an exterior surface 131 of barrier 130.

Figure 12:
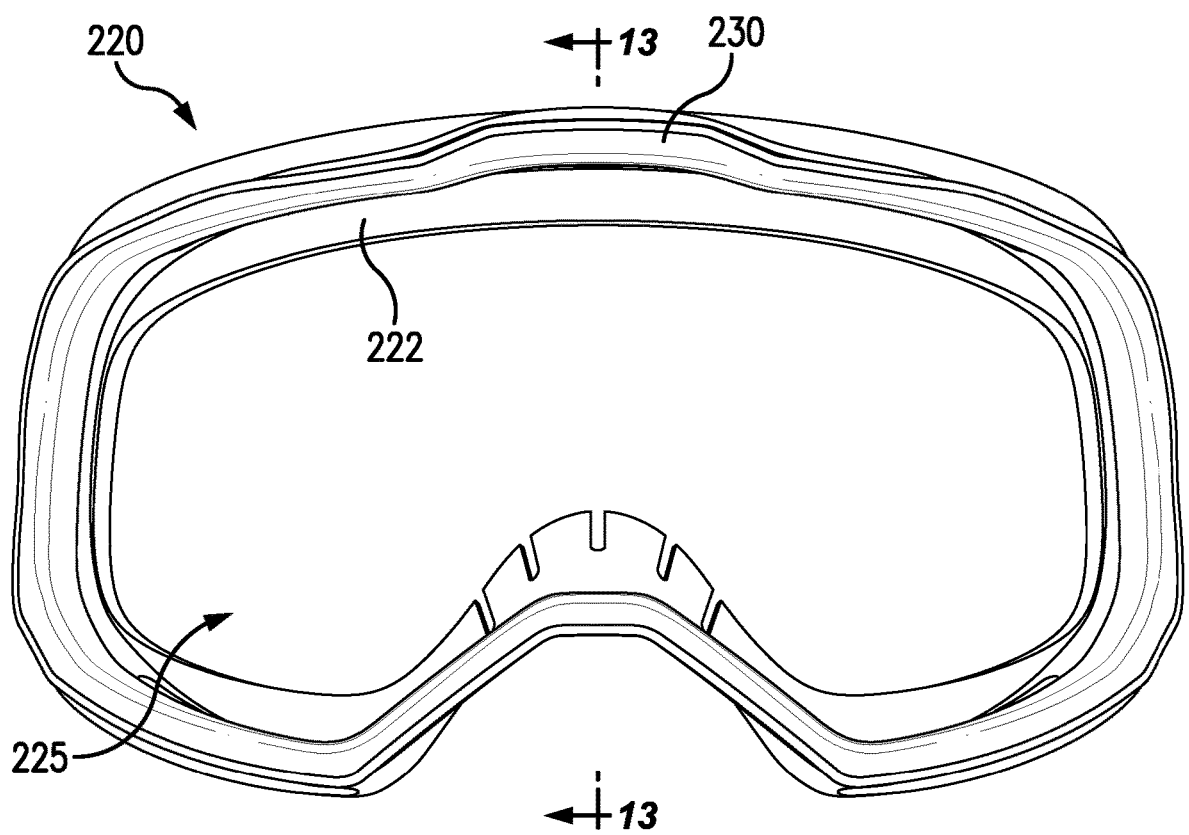
FIG. 12 shows a front view of a goggle according to an embodiment.

In some embodiments, a chassis 220 may include a barrier 230 having ridges, as shown in FIG. 12. Chassis 220 may be constructed similarly to chassis 120 as described above and differs only in the configuration of barrier 230. Thus, chassis 220 is shaped so as to contour to a wearer's face. Chassis 220 defines a central opening 225 that is covered by a lens. Chassis 220 may include a body 222 and a barrier 230. Barrier 230 may extend from an exterior facing side 221 of chassis 220 so as to contact a lens of a goggle.

Figure 13:
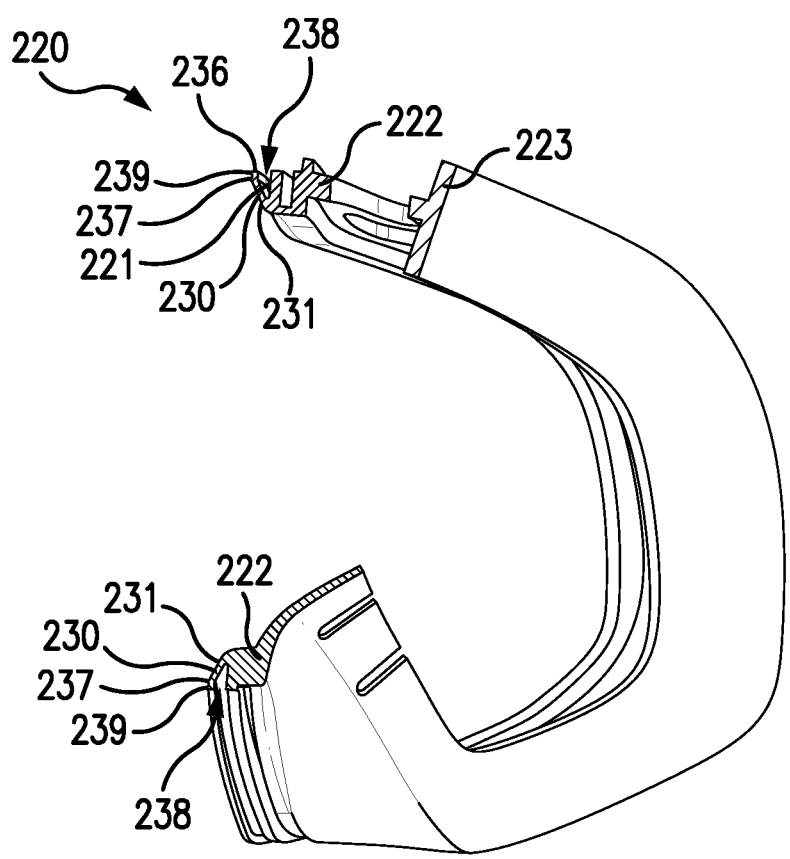
FIG. 13 shows a cross sectional view of the chassis of the goggle of FIG. 12 taken along line 13-13 as shown in FIG. 12.

As shown in FIG. 13, barrier 230 extends outwardly from an exterior facing side 221 of body 222 of chassis 220 from an inner edge 226 toward an outer edge 228. Barrier 230 may have a linear portion 235 and an end portion 236. Linear portion 235 may form an angle A relative to a vertical axis X of chassis 220 of approximately 15 to approximately 45 degrees. End portion 236 of barrier 230 may be non-linear with respect to linear portion 235, and may extend generally parallel to a vertical axis X of chassis 220.

In some embodiments, an exterior surface 231 of barrier 230 that contacts lens may include one or more ridges 237. In the embodiment of FIG. 13, barrier 230 includes two ridges 237, 239, however, it is understood that barrier 230 may include one ridge, or three or more ridges in alternate embodiments. Ridges 237, 239 extend around a perimeter of barrier 230 and may be arranged generally parallel to one another. Each ridge 237, 239 may have a separate point of contact with a lens of goggle 200 so that barrier 230 contacts lens at multiple points of contact. This helps to ensure that a seal is maintained between chassis 220 and a lens. For example, in the event ridge 237 does not contact lens, ridge 239 may maintain contact with lens, thus maintaining the seal. Adding additional ridges may further help to ensure that a seal is maintained at all times.

Figure 14:
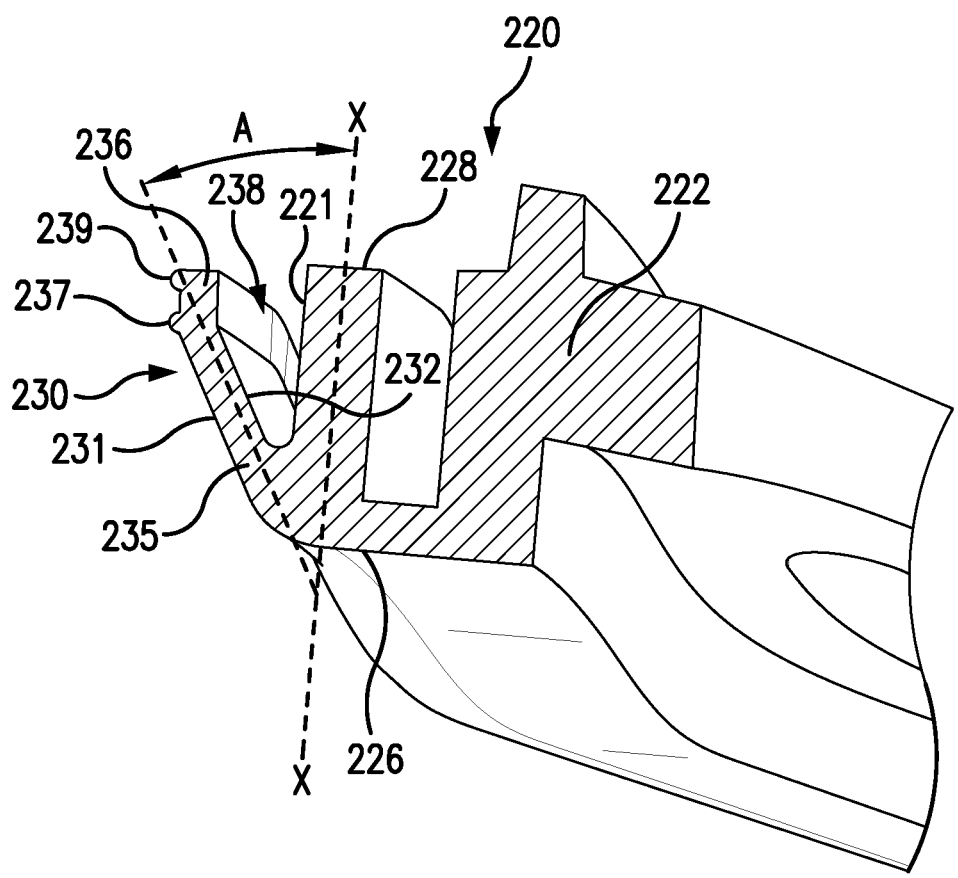
FIG. 14 shows a detailed cross sectional view of the upper end of the goggle of FIG. 12.

Barrier 230 may be arranged at an angle A relative to a vertical axis X of chassis 220, as shown in FIG. 14. A portion of barrier 230, such as linear portion 235, may form an angle A that is in a range of approximately 15 degrees to approximately 45 degrees, approximately 20 to approximately 40 degrees, or approximately 25 to approximately 35 degrees. However, as discussed above with respect to barrier 130, an angle of barrier 230 and/or a length of barrier 230 may vary around a perimeter of chassis 220.

As best shown in FIG. 14, each ridge 237, 239 may be rounded and may have a convex curvature. For example, each ridge 237, 239 may have a cross section that is semi-circular. However, it is understood that ridges 237, 239 need not be perfectly semi-circular. Further, each ridge 237, 239 may have the same shape or may differ in shape. In some embodiments, each ridge 237, 239 may have a square or triangular cross sectional area. Ridges 237, 239 may be spaced from one another and may be arranged generally parallel to one another.

Figure 15:
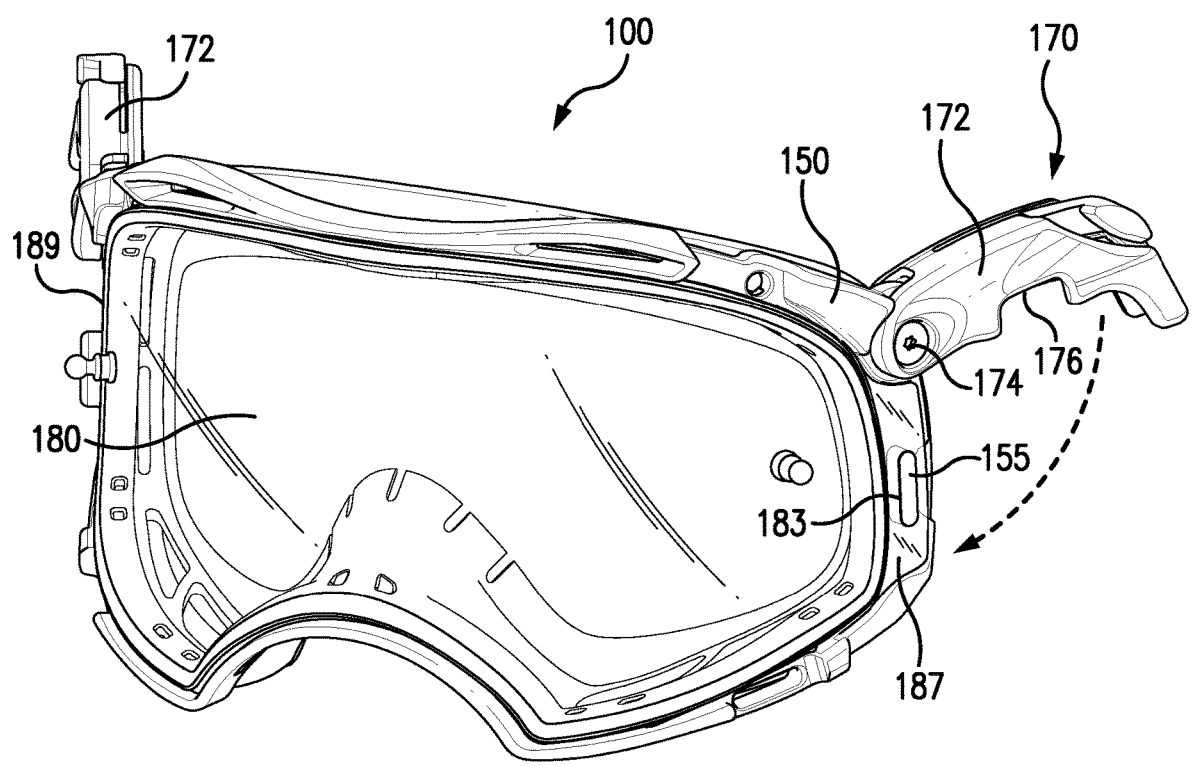
FIG. 15 shows a perspective view of a goggle having a locking assembly according to an embodiment in which the locking assembly in an open position.
Figure 16:
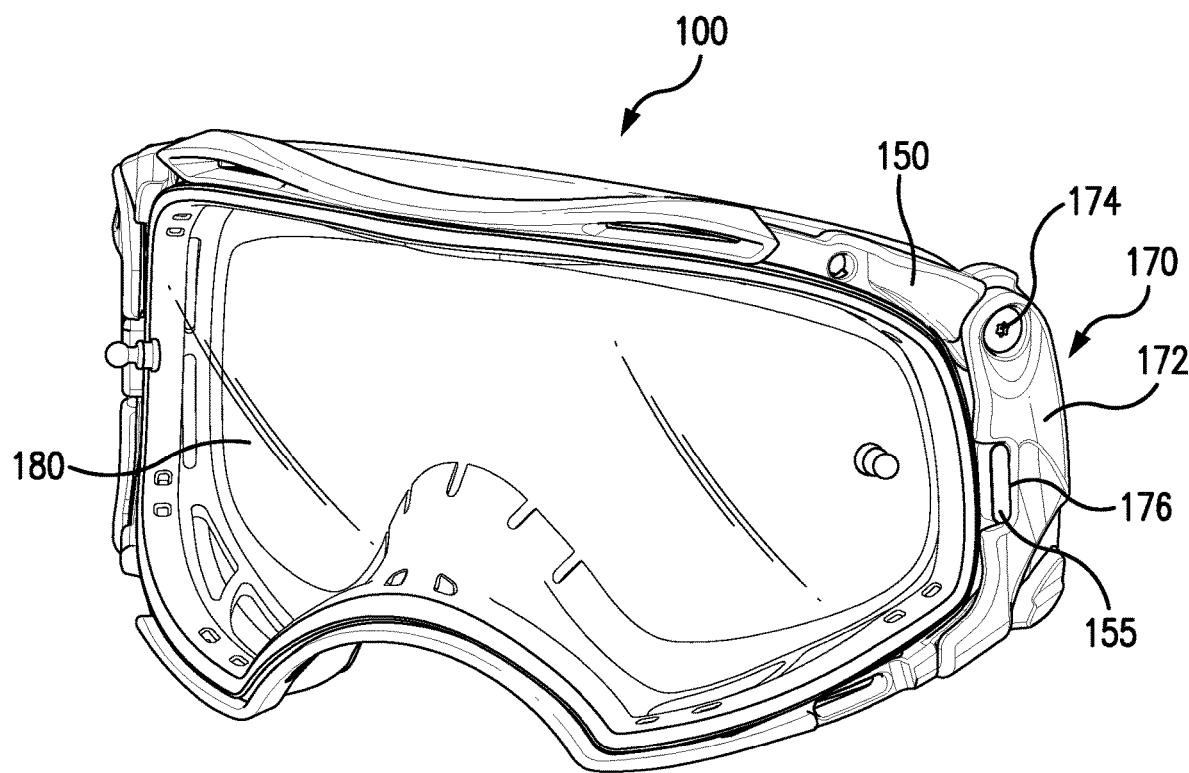
FIG. 16 shows a perspective view of the goggle having a locking assembly of FIG. 15 with the locking assembly in a closed position.

In some embodiments, goggle 100 may include a locking assembly 170 configured to removably secure lens 180 to goggle 100, as shown in FIGS. 15 and 16. When lens 180 is secured to goggle 100 via locking assembly 170, lens 180 may exert a force on barrier 130 of chassis 120 such that barrier 130 is under compression.

In some embodiments, chassis 120 or frame 150 of goggle 100 may serve as a locking assembly 170. In such embodiments, lens 180 may be secured to frame 150 via press fit, friction fit, interference fit, or by snap fit, among other removable types of connection. Frame 150 may include a recess or slot configured to receive a portion of lens 180, such as a side of lens 180 to removably secure the same to frame 150. Frame 150 may be secured to opposing sides of lens 180.

In some embodiments, as shown in FIGS. 15 and 16, locking assembly 170 may include a pair of locking arms 172. Locking arms 172 may be movably connected to frame 150 so as to move from an open, unlocked position to a closed, locked position. In the open position, locking arm 172 is rotated outward and away from lens 180 and frame 150 of goggle 100. In the closed position, locking arm 172 is rotated toward a side 187 of lens 180 and may overlay or enclose a portion of lens 180, such as a first side 187 of lens 180. In the closed position, locking arms 172 extends along frame 150 so that locking arm 172 has a continuous appearance with frame 150. A first locking arm 172 may be connected to a first side of frame 150 and is configured to secure a first side 187 of lens 180 and a second locking arm 172 may be connected to a second side of frame 150 opposite first side of frame 150 and is configured to secure a second side 189 of lens 180. First and second locking arms 172 may be connected to frame 150 via a hinge 174 or other pivot point so as to that locking arms 172 may rotate or move in a single plane. Goggle 100 may include a locking assembly as described, for example, in U.S. Pat. No. 8,881,316, which is incorporated herein by reference in its entirety.

In some embodiments, frame 150 may include a protrusion 155 configured to be received by an aperture 183 of lens 180 so as to properly position lens 180 with respect to frame 150. Further, when locking arm 172 is moved into the closed position, a cutout 176 of locking arm 172 may engage with a portion of protrusion 155 that extends through aperture 183 of lens 180 to secure lens 180 to frame 150.

It is to be appreciated that the Detailed Description section, and not the Summary and Abstract sections, is intended to be used to interpret the claims. The Summary and Abstract sections may set forth one or more but not all exemplary embodiments of the present disclosure as contemplated by the inventor(s), and thus, are not intended to limit the present disclosure and the appended claims in any way.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

What is claimed is:

1. A goggle, comprising:
a movable unitary lens having an interior surface;
a chassis, comprising:
- a body defining a central opening, wherein the body is configured to be worn on a wearer's face, the body comprising an exterior facing side that faces away from a wearer's face when worn; and
- a barrier comprising a flexible blade that is integrally formed with the body, the flexible blade comprising an interior surface facing an adjacent portion of the exterior facing side of the body,
wherein the barrier is configured to extend outwardly from the exterior facing side of the body in a direction away from the central opening, the flexible blade having an exterior surface configured to contact the interior surface of the movable unitary lens substantially along an entire perimeter of the movable unitary lens to form a seal between the central opening and the movable unitary lens,
wherein the barrier is compressed by the movable unitary lens such that the interior surface of the flexible blade is flexed toward the adjacent portion of the exterior facing side of the body.

2. The goggle of claim 1, wherein the flexible blade is connected to and extends from an inner edge of the body proximal to the central opening toward an outer edge of the body distal to the central opening.

3. The goggle of claim 1, wherein the flexible blade extends from an exterior facing side of the body of the chassis at an angle relative to a vertical axis of the goggle, wherein the angle is in a range from approximately 15 degrees to approximately 45 degrees.

4. The goggle of claim 1, wherein the flexible blade has a thickness of 0.5 mm to 1 mm as measured from an exterior surface of the flexible blade to an interior surface of the flexible blade.

5. The goggle of claim 1, wherein the chassis comprises an elastomer.

6. The goggle of claim 1, wherein the chassis comprises thermoplastic polyurethane.

7. The goggle of claim 1, wherein the chassis comprises a material having a Shore A hardness range of approximately 70 to approximately 100.

8. The goggle of claim 1, wherein the flexible blade comprises a tip that is rounded.

9. The goggle of claim 1, wherein the chassis comprises a chassis material, and further comprising a frame connected to the chassis, the frame comprising a frame material that is more rigid than the chassis material.

10. The goggle of claim 9, wherein the chassis is overmolded onto the frame.

11. The goggle of claim 1, wherein the movable unitary lens is fully removable from a frame.

12. The goggle of claim 1, further comprising a frame connected to the chassis, and a locking assembly configured to secure the movable unitary lens to the frame.

13. The goggle of claim 12, wherein the locking assembly is the frame, and wherein the movable unitary lens is secured to the frame by an interference fit.

14. The goggle of claim 1, wherein the chassis supports the movable unitary lens.

15. The goggle of claim 1, wherein the flexible blade extends upwardly from an inner edge of the body toward an adjacent outer edge of the body.

16. The goggle of claim 1, wherein the barrier is configured to contact the interior surface of the movable unitary lens adjacent a perimeter edge of the movable unitary lens.

17. A goggle, comprising:
a rigid frame comprising a frame material;
a unitary lens having an interior surface that faces toward a wearer's face when worn and an opposing exterior surface, the unitary lens being removably secured to the rigid frame;
a chassis comprising a chassis material that is less rigid than the frame material, the chassis comprising:
- a body defining a central opening, wherein the body is configured to be worn on a face of a wearer, and
- a barrier integrally formed with the body, the barrier comprising a flexible blade that detachably contacts the interior surface of the unitary lens substantially along an entire perimeter of the unitary lens so as to form a seal with the unitary lens,
wherein the rigid frame is exterior to the flexible blade such that the flexible blade is disposed between the rigid frame and the central opening.

18. The goggle of claim 17, further comprising a locking assembly configured to secure the unitary lens to the rigid frame.

19. The goggle of claim 17, wherein the flexible blade is arranged between the unitary lens and the body of the chassis.

20. The goggle of claim 17, wherein the chassis is overmolded onto the rigid frame.

21. The goggle of claim 17, wherein the unitary lens comprises two or more layers.

22. The goggle of claim 17, wherein the chassis material comprises an elastomer.

23. The goggle of claim 17, wherein the chassis material comprises thermoplastic polyurethane.

24. The goggle of claim 17, wherein the flexible blade extends outwardly from an inner edge of the body toward the rigid frame.

25. The goggle of claim 17, wherein:
the body comprises an exterior facing side that faces away from the wearer's face when worn;
the flexible blade comprises an interior surface facing the exterior facing side of the body; and
the barrier is compressed by the unitary lens such that the interior surface of the flexible blade is flexed toward the exterior facing side of the body.

* * * * *